United States Patent [19]

Tompkins et al.

[11] 4,216,425

[45] Aug. 5, 1980

[54] APPARATUS AND METHOD FOR DETECTING A SUBSTANCE IN A FLUID MEDIUM

[76] Inventors: Richard M. Tompkins, 3193 Herbell Dr., Pontiac, Mich. 48054; Jerome L. Graham, 413 Starkweather, Plymouth, Mich. 48170

[21] Appl. No.: 784,180

[22] Filed: Apr. 4, 1977

Related U.S. Application Data

[63] Continuation of Ser. No. 476,714, Jun. 5, 1974, abandoned.

[51] Int. Cl.² ............................................. G01N 27/42
[52] U.S. Cl. .................................................. 324/443
[58] Field of Search ................. 324/30 R, 30 B, 30 A, 324/62 R, 65 R, 94, 96, 133; 204/109, 195 R; 73/61.1 R, 61 R; 250/551, 373; 356/204

[56] References Cited

U.S. PATENT DOCUMENTS

| 3,272,065 | 9/1966 | Jinichi et al. | 324/96 |
| 3,340,866 | 9/1967 | Noller | 324/30 R |
| 3,384,746 | 5/1968 | Benz et al. | 250/373 |
| 3,534,354 | 10/1970 | Galginaitis | 324/133 |
| 3,731,297 | 5/1973 | Dunn et al. | 324/62 R |
| 3,875,032 | 4/1975 | Thompson | 204/109 |

*Primary Examiner*—M. Tokar
*Attorney, Agent, or Firm*—Basile & Weintraub

[57] ABSTRACT

An electronic apparatus and method for detecting a quantity of a predetermined substance disposed in a fluid medium. The apparatus includes a probe for contacting the fluid medium and for sensing an electrical condition, such as solution resistance, of the fluid medium caused at least in part by the substance to be detected. There is also included electronic control devices connected to the probe means for generating a signal which is proportional to the quantity of the substance to be detected. The signal is fed to some utilization means, such as a meter, for indicating the amount of substance in solution.

6 Claims, 5 Drawing Figures

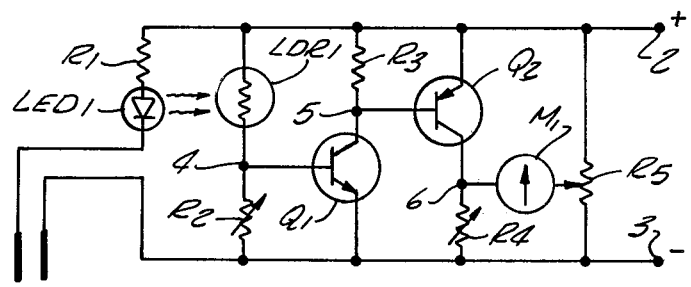
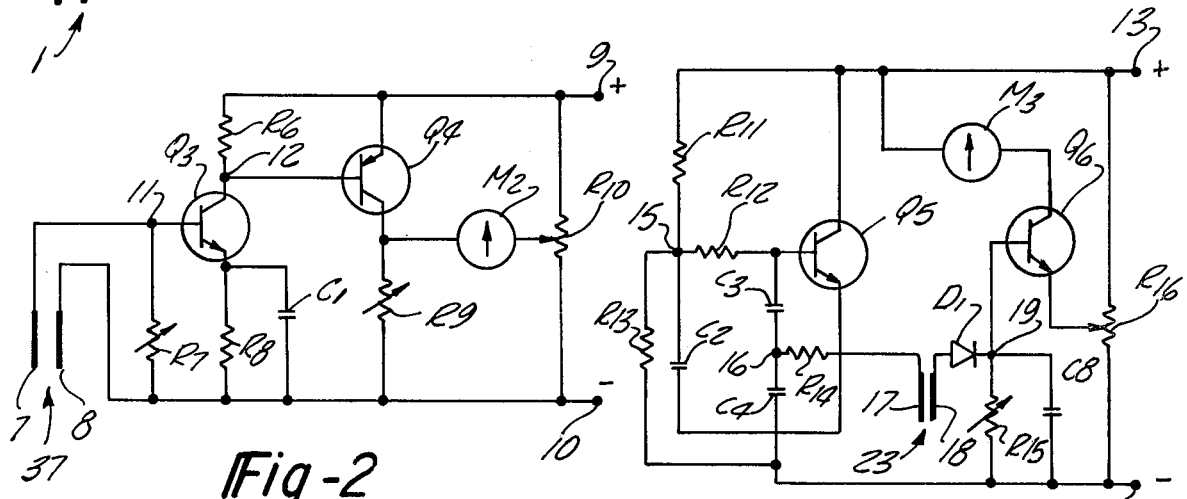
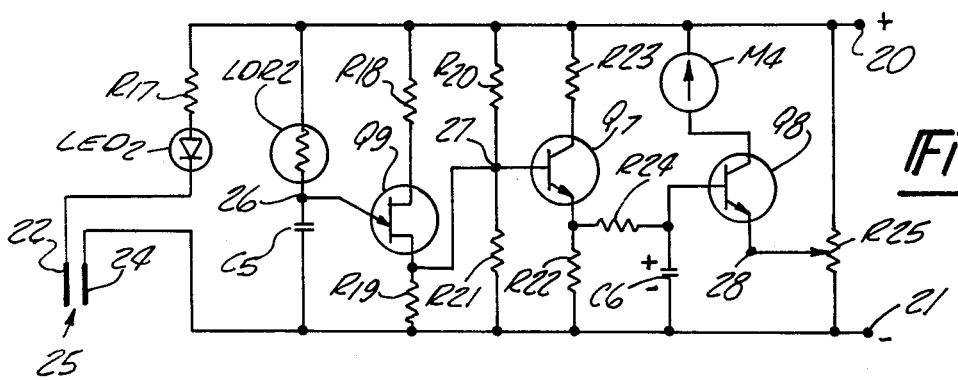
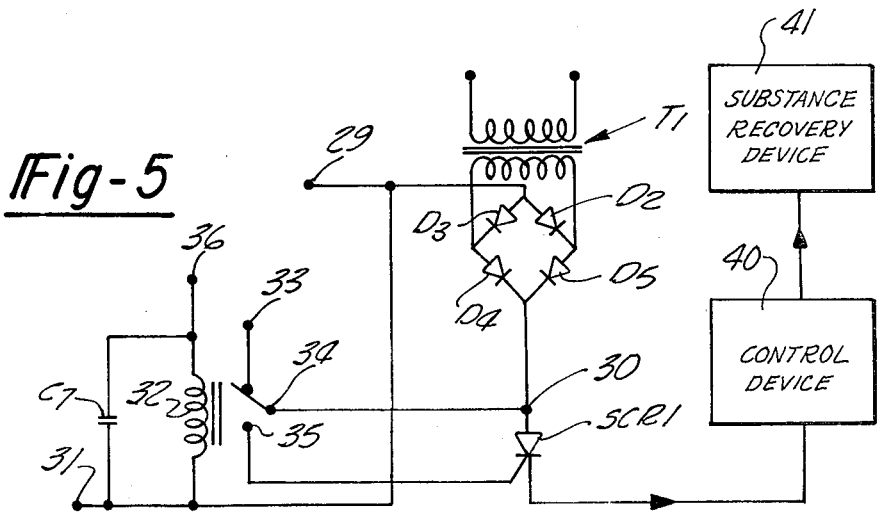

APPARATUS AND METHOD FOR DETECTING A SUBSTANCE IN A FLUID MEDIUM

This is a continuation of application Ser. No. 476,714, filed June 5, 1974 and now abandoned.

The present invention relates to an electronic apparatus and method for detecting the quantity of a predetermined substance disposed in a fluid medium. In a preferred embodiment, the present invention relates to an electronic device for measuring the number of pounds of silver in a solution, such as the type of solution used for medical X rays.

BACKGROUND OF THE INVENTION

Heretofore, some indication of substances, such as metals, in solution might be obtained by use of certain litmus-type papers which are immersed in the solution, and change appearance or color based on the substance to be detected. Such paper detectors are inaccurate, depend upon human comparison with color standards, and fail to give any accurate quantative information about the substances in solution to be measured or detected.

The present invention provides an accurate and electronic means for detecting and/or measuring the quantity of the predetermined substance in a fluid medium.

Various prior electronic devices for testing, and measuring various dielectric materials and other substances are disclosed in Burnette, Jr. U.S. Pat. No. 2,993,168, Batteau U.S. Pat. No. 3,002,150, Hopkins et al U.S. Pat. No. 3,182,255, Liu U.S. Pat. No. 3,255,412, Eckfeldt U.S. Pat. No. 2,832,734, Watrous et al U.S. Pat. No. 3,488,586, and Gnage U.S. Pat. No. 3,616,412, and British Pat. Nos. 477,849; 901,955; 1,037,627; 1,141,340; 1,167,689; and 1,203,049. However, none of these prior art disclosures and devices disclose and/or anticipate the features of the present invention which are described in greater detail hereinbelow.

SUMMARY OF THE INVENTION

The present invention provides an electronic apparatus for detecting the quantity of a predetermined substance disposed in a fluid medium. The electronic apparatus includes first means for contacting the fluid medium and for sensing an electrical condition of the fluid medium caused at least in part by the predetermined substance to be detected. The electronic apparatus also includes second means operatively and electrically connected to the first means for generating at least one signal which is substantially proportional to the quantity of the predetermined substance disposed in the fluid medium. The apparatus also includes third means operatively and electrically connected to the second means for utilizing the signal which is substantially proportional to the quantity of the predetermined substance disposed in the fluid medium.

The present invention also provides a method for detecting the quantity of a predetermined substance disposed in a fluid medium. The method includes the steps of first disposing the first means in the fluid medium for sensing an electrical condition of the fluid medium caused at least in part by the predetermined substance to be detected. A further step comprises generating from said electrical condition a signal which is substantially proportional to the quantity of the predetermined substance disposed in the fluid medium. The next step comprises feeling such generated signal to third means, such as a utilization device which may take the form of a gauge or a recovery unit.

BRIEF DESCRIPTION OF THE DRAWING

FIG. 1 illustrates a circuit diagram according to a first embodiment of the present invention.

FIG. 2 depicts a circuit diagram according to a second embodiment of the present invention.

FIG. 3 shows a circuit diagram according to a third embodiment of the present invention.

FIG. 4 illustrates a circuit diagram according to a fourth embodiment of the present invention.

FIG. 5 illustrates a combination power supply unit and control unit for governing a silver recovery unit which may be used in conjunction with any of the aforementioned embodiments of the present invention which are illustrated in FIGS. 1 thru 4.

DETAILED DESCRIPTION OF SOME PREFERRED EMBODIMENTS OF THE PRESENT INVENTION

With reference to FIG. 1, there is illustrated a first embodiment of the present invention having first means, such as probe 1, for contacting a fluid medium, such as a solution in which a predetermined substance such as silver is disposed. The probe 1 is capable of sensing the change in solution resistance.

One electrode of the probe 1 is connected to a cathode of a light-emitting diode LED 1, whose anode in turn is connected to one terminal of a current limiter resistor R1. The other terminal of the current limiting resistor R1 is connected to the positive terminal 2 of an electrical source (not shown). The electrical source may, for example, be approximately 1.5 volts. The other terminal, terminal 3, of the electrical source is connected to the other electrode of the probe 1.

A series-connected variable resistor R2 and a light detecting resistor LDR 1 are connected across terminals 2 and 3. Also connected across terminals 2 and 3 is a resistor R3 connected in series with a transistor Q1. The base of transistor Q1 is connected to terminal 4 between variable resistor R2 and light detecting resistor LDR 1.

A series connected transistor Q2 and variable resistor R4 is also connected between terminals 2 and 3 of the electrical source. The base of the transistor Q2 is connected to the terminal 5 between the resistor R3 and the collector electrode of the transistor Q1.

Also connected across the terminals 2 and 3 of the electrical source is a potentiometer R5. A meter M1 is connected to potentiometer R5 by means of a wiper contact, and is also connected to a junction 6 between the variable resistance R4 and the collector electrode of the transistor Q2.

In FIG. 1, the probe 1 constitutes the first means for contacting the aforesaid fluid medium and for sensing the electrical condition of the fluid medium caused at least in part by the predetermined substance to be detected.

All of the remaining components illustrated in FIG. 1, with the exception of meter M1 and potentiometer R5, constitute the aforementioned second means which is operatively and electrically connected to the first means for generating at least one signal which is substantially proportional to the quantity of the predetermined substance, such as silver, disposed in the fluid medium.

The meter M1 and the potentiometer R5 constitute third means which are operatively and electrically connected to the second means for utilizing the signal which is substantially proportional to the quantity of the predetermined substance disposed in the fluid medium.

In the embodiment illustrated in FIG. 1, the resistor R1 serves as a current limiter for the light emitting diode LED 1 and sets its operating point. The probe 1, by sensing a change in the solution resistance, and acting as a variable resistance in series with the light emitting diode LED 1, limits the current flowing through the light emitting diode LED 1, and consequently varies the light output of the light emitting diode LED 1. This changing light level is detected or sensed by the light detecting resistor LDR 1, which in turn varies the bias placed on the base electrode of the transistor Q1.

The variable resistor R2 sets the operating bias of the transistor Q1. As the conduction of the transistor Q1 varies, the bias supplied to the base electrode of transistor Q2 also varies. The transistor Q2 is biased to operate as an amplifier.

The varying conduction of transistor Q2 is indicated on the meter M1, and the indication on the meter M1 is proportional to the amount of silver in the solution being tested. The meter M1 is calibrated to read, for example, in ounces of silver per gallon of solution. The potentiometer R5 functions as a meter zero adjusting element. In a particular working embodiment of the invention, the meter M1 was calibrated to read from 0–2 indicating the ounces of silver per gallon of solution being tested. In such a working embodiment, a meter reading of "1" indicates one ounce of silver per gallon.

With reference to FIG. 2, there is shown a second embodiment of the present invention wherein the probe electrodes are formed from dissimilar materials. Probe electrode 7 is connected to the base of transistor Q3, and the other probe electrode 8, formed of a substance different than the substance of probe 7, is connected to the negative terminal 10 of an electrical source (not shown). A resistor R6 is connected between the collector electrode of transistor Q3 and the other terminal 9 of the electrical source.

A variable resistor R7 is connected between terminal 10 of the electrical source and terminal 11 at the base of the transistor Q3. The parallel combination of a resistor R6 and a capacitor C1 is connected between the terminal 10 and the emitter electrode of the transistor Q3.

A series connected transistor Q4 and a variable resistor R9 is also connected between the terminals 9 and 10 of the electrical source. The base of the transistor Q4 is connected to a terminal 12 intermediate to resistor R6 and the collector electrode of the transistor Q3.

A combination meter M2 and a zero adjust potentiometer R10, similar to the combination of meter M1 and zero adjust R5 of the FIG. 1 embodiment, is also connected between terminals 9 and 10 of the electrical source.

The circuit of the embodiment illustrated in FIG. 2 functions essentially similar to a voltmeter. The dissimilar materials used in the probe electrodes 7 and 8, when immersed in a solution or electrolyte, generate a voltage. For example, the probe electrode 7 may be made from carbon, and the probe electrode 8 may be made from steel. Various other combinations of probe electrode dissimilar materials are also within the scope of the present invention.

The resistors R6, R7 and R8 set the operating point of the transistor Q3 which serves to amplify the voltage generated between the probe electrodes 7 and 8. This amplified voltage is coupled to the transistor Q4, which further amplifies it and this amplified signal is in turn indicated on the meter M2. In essence, the more metal that is in the solution being tested, the greater the current flow across the probe electrodes 7 and 8 due to a decrease in the solution resistance. Any variation is read directly by the meter M2.

FIG. 3 illustrates a third embodiment of the present invention. In FIG. 3, the positive terminal 13 of an electrical source (not shown) is connected to a resistor R11, which in turn is connected to one terminal of a capacitor C2. The other terminal of the capacitor C2 is connected to the emitter electrode of a transistor Q5. The collector electrode of the transistor Q5 is connected to terminal 13.

A resistor R13 is connected between the other terminal of the electrical source and a terminal 15 intermediate resistor R11 and capacitor 2. A resistor R12 is connected between the base electrode of transistor Q5 and terminal 15 intermediate resistor R11 and capacitor C2.

Series connected capacitors C3 and C4 are connected between the terminal 14 and the base electrode of the transistor Q5. A resistor R14 has one of its terminals connected to terminal 16 intermediate capacitors C3 and C4, and has its other terminal connected to electrode 17 of a probe 23. The other electrode 18 of the probe 23 is connected to the anode of a diode D1 whose cathode is connected to terminal 19 of the base electrode of a transistor Q6.

A meter M3 is connected between terminal 13 and the collector electrode of transistor Q6. A meter zero adjust potentiometer R16 is connected across terminals 13 and 14, and the wiper contact of potentiometer R16 is connected to the emitter electrode of transistor Q6.

A variable resistor R15 is connected in parallel with a capacitor C8 between terminals 14 and 19. This parallel combination of resistor R15 and capacitor C8 functions as a filter and bias network for the transistor Q6.

In the embodiment of the invention illustrated in FIG. 3, the transistor Q5 and the resistors R11, R12, R13 and R14 together with the capacitors C2, C3 and C4 constitutes a phase-shift oscillator. The output signal from this phase-shift oscillator section is fed to the diode D1 through the probe 23 which is immersed in the solution being tested. The varying resistance of the solution acts as a series-limiting resistance which varies the amplitude of the electrical signal reaching the diode D1.

The signal applied to the diode D1 is rectified by the diode D1, and is then filtered by the resistor R15-capacitor C8 combination which also acts as a bias network for the transistor Q6. This varying signal controls the conduction of the transistor Q6 which, in turn, drives the meter M3. The invention also contemplates variations where such signal controls the conduction of the transistor Q6 which, instead of driving a meter M3, may drive a relay or any indicating, control or utilization device to control, for example, a silver recovery apparatus.

With reference to FIG. 4, there is shown a fourth embodiment of the present invention wherein a resistor R17, a light emitting diode LED 2 and a probe 25 are connected in series across the terminals 20 and 21 of an electrical source. Probe electrode 22 is connected to the cathode of the light emitting diode LED 2, and probe electrode 24 is connected to the negative terminal 21 of the electrical source.

A capacitor C5 connected in series with light detecting resistor LDR 2 is connected across terminals 20 and 21. Also connected across the terminals 20 and 21 is a resistor R18 connected to one electrode of a unijunction transistor Q9, and a resistor R19 connected to another electrode of unijunction transistor Q9. The third electrode of the unijunction transistor Q9 is connected to terminal 26 intermediate capacitor C5 and light detecting resistor LDR 2. Series connected resistors R20 and R21 are also connected between terminals 20 and 21. Terminal 27 intermediate resistors R20 and R21 is connected to the junction between resistor R19 and unijunction transistor Q9.

Terminal 27 is connected to the base of a transistor Q7. A resistor R23 is connected between terminal 20 and the collector electrode of transistor Q7. A resistor R22 is connected between terminal 21 and the emitter electrode of transistor Q7.

A resistor R24 is connected between the emitter electrode of transistor Q7 and the base electrode of a transistor Q8. A meter M4 is connected between the terminal 20 and the collector electrode of transistor Q8. A capacitor C6 is connected between terminal 21 and the base electrode of transistor Q8.

A meter zero adjust potentiometer 25 is connected between terminals 20 and 21. The wiper terminal 28 of the zero adjust potentiometer R25 is connected to the emitter electrode of transistor Q8.

In the circuit shown in FIG. 4, the resistor R17 serves as a current limiter for the light emitting diode LED 2 and serves also to set the operating point of the light emitting diode LED 2. The probe 25, by sensing a change in solution resistance, and acting as a variable resistance in series with the light emitting diode LED 2, limits the current flowing through the light emitting diode LED 2. Consequently, this limits and varies the light output of the light emitting diode LED 2.

This change in light output is sensed by the light detecting resistor LDR 2 which, in conjunction with the capacitor C5, varies the frequency of the unijunction transistor Q9. This frequency change is fed to the transistor Q7 where it is amplified, filtered by the resistor R22-capacitor C6 combination, and then used to drive the transistor Q8. The meter M4 thereby indicates the change in frequency caused by the varying resistance of the solution under test.

FIG. 5 shows a combination power supply unit and a control unit for governing equipment for recovering the predetermined substance disposed in the fluid medium, and the FIG. 5 embodiment may be used in conjunction with any of the aforementioned embodiments. For example, if the FIG. 5 circuitry were to be used in conjunction with the FIG. 1 embodiment, then the FIG. 5 circuitry would replace the electrical source of FIG. 1, and components M1, R5 and R4. In other words, terminal 36 in FIG. 5 would be connected to terminal 6 of FIG. 1, terminal 29 or 31 (actually the same electrical terminal) of FIG. 5 would take the place of the negative terminal 3 of FIG. 1, and terminal 30 of FIG. 5 would take the place of positive terminal 2 in FIG. 1.

FIG. 5 shows a transformer T1 connected to a full-wave rectifier composed of diodes D2, D3, D4 and D5. Terminal 30 represents the positive terminal of the full-wave rectifier, and terminal 29 (or 31) represents the negative terminal of the full-wave rectifier.

A parallel combination of a capacitor C7 and a relay coil 32 is connected between negative terminal 31 and a terminal 36. The relay coil 32 controls a switching element 34 for connecting between the terminals 33 and 35. Positive terminal 30 of the full-wave rectifier is connected to switching element 34, and is also connected to one electrode of a silicone controlled rectifier SCR 1. Another electrode of the silicone controlled rectifier SCR 1 is connected to terminal 35. The remaining electrode of SCR 1 may be used for connection to a silver recovery apparatus, comprising, for example, a substance recovery device 41 controlled by a control device 40. In other words, the circuitry shown in FIG. 5 and the mentioned silver recovery unit can be used in place of the meter and zero adjust shown in FIG. 1 or comparable third means shown in the other embodiments.

We claim:

1. An electronic apparatus for substantially instantaneously detecting the quantity of a predetermined substance disposed in a fluid medium, comprising, in combination:
    first means for contacting said fluid medium and for sensing an electrical condition of said fluid medium caused at least in part by said predetermined substance to the detected, said first means including a probe for sensing a change in the resistance of said fluid medium;
    second means operatively and electrically connected to said first means for generating substantially instantaneously at least one signal which is substantially proportional to said quantity of said predetermined substance disposed in said fluid medium, said second means including a light emitting diode connected in series with said probe;
    third means operatively and electrically connected to said second means for utilizing substantially instantaneously said signal which is substantially proportional to said quantity of said predetermined substance disposed in said fluid medium, said third means including a meter calibrated to read substantially instantaneously the amount of the predetermined substance to be detected;
    and said probe, by sensing a change in the resistance of said fluid medium, acts as a variable resistance in series with said light emitting diode, thereby varying its light output which in turn substantially instantaneously controls the indication on said meter, said indication being proportional to the amount of the predetermined substance disposed in said fluid medium.

2. An electronic apparatus according to claim 1 wherein:
    said second means includes a phase-shift oscillator which controls the conduction of an amplifier;
    said meter of said third means is driven and controlled by the conduction of said amplifier; and
    whereby a signal from said phase-shift oscillator is fed through said probe immersed in said fluid medium and acts as a series-limited resistance which varies the amplitude of the signal reaching the amplifier, said signal controlling the conduction of the amplifier which in turn drives the meter to give an indication of the amount of said predetermined substance in said fluid medium.

3. An electronic apparatus according to claim 1 wherein:
    said light emitting diode of said second means is operatively disposed in proximity to a light detecting resistor which, in turn, is electrically and operatively connected to an amplifier;

said meter of said third means is electrically connected to the output of said amplifier;

said probe, by sensing a change in the resistance of said fluid medium, limits the current flowing through said light emitting diode and thus varies its light output; and said amplifier is controlled by the light output sensed by the light detecting resistor, and the conduction of said amplifier is used to control the indication of said meter.

4. An electronic apparatus according to claim 3, including:

first impedance means which serves as a current limiter for said light emitting diode;

a first electronic control device operatively and electrically connected to said light detecting resistor;

a second electronic control device operatively connected to said first electronic control device;

a third electronic control device operatively connected to said second electronic control device and to said meter;

whereby the change in light output sensed by the light detecting resistor varies the frequency of said first electronic control device, and this frequency change is fed to said second electronics control device where it is amplified, filtered and used to drive said third electronic control device, and thus said meter indicates the change in frequency caused by the variation in resistance of the fluid medium under test.

5. An electronic apparatus according to claim 1 wherein said third means includes a device for recovering said predetermined substance from said fluid medium, and a second device for controlling the operation of said recovery device.

6. An electronic apparatus according to claim 2 wherein said third means includes a device for recovering said predetermined substance from said fluid medium, and a second device for controlling the operation of said recovery device.

* * * * *